United States Patent
Welch et al.

(10) Patent No.: US 7,009,051 B2
(45) Date of Patent: Mar. 7, 2006

(54) 4-(2-PYRIDYL) PIPERAZINES HAVING 5HT7 RECEPTOR AGONIST ACTIVITY

(75) Inventors: Willard M. Welch, Mystic, CT (US); Vinod Parikh, Mystic, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/617,967

(22) Filed: Jul. 10, 2003

(65) Prior Publication Data

US 2004/0014769 A1   Jan. 22, 2004

Related U.S. Application Data

(63) Continuation of application No. 10/075,910, filed on Feb. 13, 2002, now abandoned.

(60) Provisional application No. 60/288,178, filed on May 2, 2001, provisional application No. 60/289,466, filed on May 8, 2001.

(51) Int. Cl.
*A61K 31/496* (2006.01)
*C07D 401/14* (2006.01)
(52) U.S. Cl. .................. 544/363; 544/364; 514/253.06; 514/253.12
(58) Field of Classification Search ........ 544/363–364; 514/253.06, 253.12
See application file for complete search history.

(56) References Cited

OTHER PUBLICATIONS

Mullins et al. Medline Abstract for Neuropsychopharmacology (1999), vol. 21, p. 352-367.*
Vanhoenacker et al. TIPS, vol. 21, p. 70-77 (2000).*

\* cited by examiner

*Primary Examiner*—Emily Bernhardt
(74) *Attorney, Agent, or Firm*—Steve T. Zelson; Jolene W. Appleman

(57) ABSTRACT

The present invention relates to compounds of the formula I

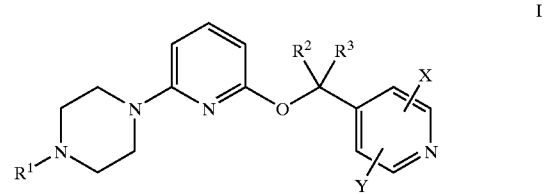

wherein $R^1$, $R^2$, $R^3$, X and Y are defined as in the specification. Those compounds are 5HT7 partial agonists and are useful in the treatment of several disorders of the central nervous system.

1 Claim, No Drawings

4-(2-PYRIDYL) PIPERAZINES HAVING 5HT7 RECEPTOR AGONIST ACTIVITY

CROSS REFERENCE TO PRIOR APPLICATIONS

This application is a Continuation of application Ser. No. 10/075,910, filed on Feb. 13, 2002, now abandoned, which claims the benefit of Provisional application Nos. 60/288,178, filed on May 2, 2001, and 60/289,466 filed on May 8, 2001.

BACKGROUND OF THE INVENTION

The present invention relates to novel 4-(2-pyridyl)piperizines, to pharmaceutical compositions containing them and to their medicinal use. The compounds of the present invention are potent and selective partial agonists at serotonin 7 (5-HT7) receptors, and are capable of modulating circadian rhythms. They are useful in treating treatment of depression, anxiety, migraine, and eating disorders, as well as disorders or conditions the treatment which can be effected or facilitated by altering circadian rhythms. Examples of such disorders and conditions are seasonal affective disorder, bipolar disorder, jet lag, sleep disorders such as circadian sleep rhythms disorder, sleep deprivation, REM sleep disorders, hypersomnia, parasomnias, sleep-wake cycle disorders, narcolepsy, sleep disorders associated with blindness, sleep disorders associated with obesity, and sleep disorders associated with shift work or irregular work schedules; nocturnal enuresis, and restless legs syndrome.

Serotonin 7 receptors are present in the suprachiasmatic nucleus (SCN), the brain region that contains the biological clocks, and their activation leads to a resetting of the clocks as a function of dose and timing of treatment. Such a mechanistic link is evident in numerous paradigms—in in vitro electrophysiological studies of SCN neuronal activity, and in light induced changes in wheel running behavior and nighttime melatonin suppression—in each case activation of 5HT7 receptors having the potential to modulate both clock function and the clock resetting ability of light. Full agonists and partial agonists of the 5HT7 receptor therefore offer a wide range of clinically useful therapeutics.

The present invention also relates to a method of treating depression or anxiety in a mammal, including a human, by administering to the mammal a 5HT7 partial agonist in combination with an antidepressant or an anxiolytic agent. It also relates to pharmaceutical compositions containing a pharmaceutically acceptable carrier, a 5HT7 partial agonist and an anxiolytic agent or antidepressant.

The connection between the 5-HT7 receptor and CNS disease such as depression and circadian rhythm disorders has been disclosed in a number of publications, including Lopez-Rodriguez, et. al., Bioorg. Med. Chem. Lett., 10 (2000) 1097–1100.

Glennon's article "Serotonin Receptors: Clinical Implications", *Neurscience and Behavioral Reviews*, 14, 35–47 (1990), refers to the pharmacological effects associated with serotonin receptors including appetite suppression, thermoregulation, cardiovascular/hypotensive effects, sleep, psychosis, anxiety, depression, nausea, emesis, Alzheimer's disease, Parkinson's disease and Huntington's disease.

Serotonin 7 partial agonists are useful for the treatment of depression. As used herein, the term "depression" includes depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; a typical depression (or reactive depression) including increased appetite, hypersomnia, psychomotor agitation or irritability, anxiety and phobias, seasonal affective disorder, or bipolar disorders or manic depression, for example, bipolar I disorder, bipolar II disorder and cyclothymic disorder.

Other mood disorders encompassed within the term "depression" include dysthymic disorder with early or late onset and with or without a typical features; dementia of the Alzheimer's type, with early or late onset, with depressed mood; vascular dementia with depressed mood, disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood.

Encompassed within the term "depression" are: depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression.

Major depression is characterized by feelings of intense sadness and despair, mental slowing and loss of concentration, pessimistic worry, agitation, and self-deprecation. Physical changes also occur, especially in severe or "melancholic" depression. These include insomnia or hypersomnia, anorexia and weight loss (or sometimes overeating), decreased energy and libido, and disruption of normal circadian rhythms of activity, body temperature, and many endocrine functions.

Treatment regimens for depression commonly include the use of tricyclic antidepressants, monoamine oxidase inhibitors, some psychotropic drugs, lithium carbonate, and electroconvulsive therapy (ECT) (see R. J. Baldessarini in *Goodman & Gilman's The Pharmacological Basis of Therapeutics*, 9th Edition, Chapter 19, McGraw-Hill, 1996 for a review). More recently, new classes of antidepressant drugs are being developed including selective serotonin reuptake inhibitors (SSRIs), specific monoamine reuptake inhibitors and 5-HTIA receptor agonists, antagonists and partial agonists.

Serotonin 7 partial agonists are also useful for the treatment of anxiety. As used herein, the term "anxiety" includes anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalized anxiety disorders.

"Generalized anxiety" is typically defined as an extended period (e.g., at least six months) of excessive anxiety or worry with symptoms on most days of that period. The anxiety and worry is difficult to control and may be accompanied by restlessness, being easily fatigued, difficulty concentrating, irritability, muscle tension, and disturbed sleep.

"Panic disorder" is defined as the presence of recurrent panic attacks followed by at least one month of persistent concern about having another panic attack. A "panic attack" is a discrete period in which there is a sudden onset of intense apprehension, fearfulness or terror. During a panic attack, the individual may experience a variety of symptoms including palpitations, sweating, trembling, shortness of breath, chest pain, nausea and dizziness. Panic disorder may occur with or without agoraphobia.

"Phobias" includes agoraphobia, specific phobias and social phobias. "Agoraphobia" is characterized by an anxiety about being in places or situations from which escape might be difficult or embarrassing or in which help may not be available in the event of a panic attack. Agoraphobia may occur without history of a panic attack. A "specific phobia" is characterized by clinically significant anxiety provoked by feared object or situation. Specific phobias include the following subtypes: animal type, cued by animals or insects; natural environment type, cued by objects in the natural environment, for example storms, heights or water; blood-injection-injury type, cued by the sight of blood or an injury or by seeing or receiving an injection or other invasive medical procedure; situational type, cued by a specific situation such as public transportation, tunnels, bridges, elevators, flying, driving or enclosed spaces; and other type where fear is cued by other stimuli. Specific phobias may also be referred to as simple phobias. A "social phobia" is characterized by clinically significant anxiety provoked by exposure to certain types of social or performance circumstances. Social phobia may also be referred to as social anxiety disorder.

Other anxiety disorders encompassed within the term "anxiety" include anxiety disorders induced by alcohol, amphetamines, caffeine, cannabis, cocaine, hallucinogens, inhalants, phencychdine, sedatives, hypnotics, anxiolytics and other substances, and adjustment disorders with anxiety or with mixed anxiety and depression.

Anxiety may be present with or without other disorders such as depression in mixed anxiety and depressive disorders. The compositions of the present invention are therefore useful in the treatment of anxiety with or without accompanying depression.

Anxiety disorders are generally treated using benzodiazepine sedative-antianxiety agents. Potent benzodiazepines are effective in panic disorder as well as in generalized anxiety disorder, however, the risks associated with drug dependency may limit their long-term use. 5-HT$_{1A}$ receptor partial agonists also have useful anxiolytic and other psychotropic activity, and less likelihood of sedation and dependence (see R. J. Baldessarini in *Goodman & Gilman's Tite Pharmacological Basis of Therapeutics,* 9th Edition, Chapter 18, McGraw-Hill, 1996 for a review).

SUMMARY OF THE INVENTION

The present invention relates to compounds of the formula I

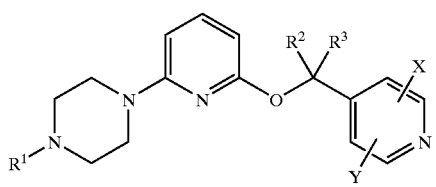

I wherein $R^1$ is hydrogen, $(C_1-C_6)$alkyl, aryl, heteroaryl, arylmethyl or heteroarylmethyl, wherein said aryl and heteroaryl and the aryl and heteroaryl moieties of said arylmethyl and said heteroarylmethyl can optionally be substituted with one or more substituents, preferably with from zero to two substituents, independently selected from hydrogen, halo, hydroxy, nitro, amino, cyano, —C(=O)—O— $(C_1-C_6)$alkyl, —$(C_1-C_6)$alkyl-C(=O)—$(C_1-C_6)$alkyl, —C(=O)H, —C(=O)NR$^4$R$^5$), $(C_1-C_6)$alkyl optionally substituted with from one to three fluorine atoms, and $(C_1-C_6)$alkoxy optionally substituted with from one to three fluorine atoms;

$R^2$ and $R^3$ are independently selected from hydrogen and $(C_1-C_6)$alkyl; or $R^2$ and $R^3$, taken together, may form a saturated carbocyclic ring containing from 3 to 6 ring carbon atoms;

$R^4$ and $R^5$ are independently selected from hydrogen and $(C_1-C_6)$alkyl; or $R^4$ and $R^5$, taken together, may form a saturated carbocyclic ring containing from 3 to 6 ring carbon atoms; and X and Y are independently selected from hydrogen, halo, hydroxy, nitro, amino, cyano, —C(=O)—O—$(C_1-C_6)$alkyl, $(C_1-C_6)$alkyl-C(=O)—$(C_1-C_6)$alkyl, —C(=O)H, —C(=O)NR$^4$R$^5$),$(C_1-C_6)$ alkyl optionally substituted with from one to three fluorine atoms, and $(C_1-C_6)$alkoxy optionally substituted with from one to three fluorine atoms;

and the pharmaceutically acceptable salts of such compounds.

Preferred compounds of the formula I are those wherein $R^1$ is hydrogen and X and Y are selected from hydrogen and methyl.

More specific embodiments of this invention relate to compounds of the formula I wherein one of $R^2$ and $R^3$ is hydrogen and the other of $R^2$ and $R^3$ is other than hydrogen.

Other more specific embodiments of this invention relate to compounds of the formula I wherein both $R^2$ and $R^3$ are hydrogen.

Other more specific embodiments of this invention relate to the following compounds and their pharmaceutically acceptable salts:

1-[6-(Pyridin-4-ylmethoxy)-pyridin-2-yl]-piperazine;

3-{4-[6-(Pyridin-4-ylmethoxy)-pyridin-2-yl]-piperazin-1-yl}-propan-1-ol;

1-Methyl-4-[6-(pyridin-4-ylmethoxy)-pyridin-2-yl]-piperazine;

1-Ethyl-4-[6-(pyridin-4-ylmethoxy)-pyridin-2-yl]-piperazine;

1-Benzyl-4-[6-(pyridin-4-ylmethoxy)-pyridin-2-yl]-piperazine;

1-Propyl-4-[6-(pyridin-4-ylmethoxy)-pyridin-2-yl]-piperazine;

1-(2-Methoxy-ethyl)-4-[6-(pyridin-4-ylmethoxy)-pyridin-2-yl]-piperazine;

1-Benzo[1,3]dioxol-5-ylmethyl-4-[6-(pyridin-4-ylmethoxy)-pyridin-2-yl]-piperazine;

1-(2-Phenoxy-ethyl)-4-[6-(pyridin-4-ylmethoxy)-pyridin-2-yl]-piperazine;

1-(3-Phenoxy-propyl)4-[6-(pyridin-4-ylmethoxy)-pyridin-2-yl]-piperazine;

1-(3-Phenyl-propyl)-4-[6-(pyridin-4-ylmethoxy)-pyridin-2-yl]-piperazine;

1-Butyl-4-[6-(pyridin-4-ylmethoxy)-pyridin-2-yl]-piperazine;

3-{4-[6-(Pyridin-4-ylmethoxy)-pyridin-2-yl]-piperazin-1-yl}-propionitrile;

4-{4-[6-(Pyridin-4-ylmethoxy)-pyridin-2-yl]-piperazin-1-yl}-butyronitrile;

1-(3-Methyl-benzyl)-4-[6-(pyridin-4-ylmethoxy)-pyridin-2-yl]-piperazine;

1-(3-Chloro-benzyl)-4-[6-(pyridin-4-ylmethoxy)-pyridin-2-yl]-piperazine;

3-{4-[6-(Pyridin-4-ylmethoxy)-pyridin-2-yl]-piperazin-1-ylmethyl}-benzonitrile;

2-{4-[6-(Pyridin-4-ylmethoxy)-pyridin-2-yl]-piperazin-1-ylmethyl}-benzonitrile;

4-{4-[6-(Pyridin-4-ylmethoxy)-pyridin-2-yl]-piperazin-1-ylmethyl}-benzonitrile;

1-(3-Fluoro-benzyl)-4-[6-(pyridin-4-ylmethoxy)-pyridin-2-yl]-piperazine;

1-(4-Fluoro-benzyl)-4-[6-(pyridin-4-ylmethoxy)-pyridin-2-yl]-piperazine;

1-(3-Methoxy-benzyl)-4-[6-(pyridin-4-ylmethoxy)-pyridin-2-yl-piperazine;

1-(2-Chloro-benzyl)-4-[6-(pyridin-4-ylmethoxy)-pyridin-2-yl]-piperazine;

1-(4-tert-butyl-benzyl)-4-[6-(pyridin-4-ylmethoxy)-pyridin-2-yl]-piperazine;

1-(2-Fluoro-benzyl)-4-[6-(pyridin-4-ylmethoxy)-pyridin-2-yl]-piperazine;

1-(2-Bromo-benzyl)-4-[6-(pyridin-4-ylmethoxy)-pyridin-2-yl]-piperazine;

1-Isopropyl-4-[6-(pyridin-4-ylmethoxy)-pyridin-2-yl]-piperazine;

1-Cyclopropyl-4-[6-(pyridin-4-ylmethoxy)-pyridin-2-yl]-piperazine;

1-(1-Methyl-hexyl)-4-[6-(pyridin-4-ylmethoxy)-pyridin-2-yl]-piperazine;

1-[6-(2-Methyl-pyridin-4-ylmethoxy)-pyridin-2-yl]-piperazine;

1-[6-(2-Methyl-pyridin-4-ylmethoxy)-pyridin-2-yl]-piperazine;

4-(6-Piperazin-1-yl-pyridin-2-yloxymethyl)-quinoline;

1-[6-(3-Methyl-pyridin-4-ylmethoxy)-pyridin-2-yl]-piperazine;

1-[6-(2-Phenyl-pyridin-4-ylmethoxy)-pyridin-2-yl]-piperazine;

1-[6-(2,6-Dimethyl-pyridin-4-ylmethoxy)-pyridin-2-yl]-piperazine; and 1-(4-Fluoro-benzyl)-4-[6-(pyridin-4-ylmethoxy)-pyridin-2-yl]-piperazine.

The present invention also relates to a pharmaceutical composition for treating a disorder or condition selected from depression, anxiety avoidant personality disorder, premature ejaculation, eating disorders (eq., anorexia nervosa and bulimia nervosa), migraine, premenstrual syndrome, premenstrual dysphoric disorder, seasonal affective disorder, bipolar disorder, jet lag, sleep disorders such as circadian sleep rhythms disorder, sleep deprivation, REM sleep disorders, hypersomnia, parasomnias, sleep-wake cycle disorders, narcolepsy, sleep disorders associated with blindness, sleep disorders associated with obesity, and sleep disorders associated with shift work or irregular work schedules; nocturnal enuresis, and restless legs syndrome in a mammal, preferably a human, comprising an amount of a compound of the formula I or a pharmaceutically acceptable salt thereof effective in treating such disorder or condition and a pharmaceutically acceptable carrier.

The present invention also relates to a method for treating a disorder or condition selected from depression, anxiety, avoidant personality disorder, premature ejaculation, eating disorders (e.g., anorexia nervosa and bulimia nervosa), migraine, premenstrual syndrome, premenstrual dysphoric disorder, seasonal affective disorder, bipolar disorder, jet lag, sleep disorders such as circadian sleep rhythms disorder, sleep deprivation, REM sleep disorders, hypersomnia, parasomnias, sleep-wake cycle disorders, sleep disorders associated with blindness, sleep disorders associated with obesity, narcolepsy and sleep disorders associated with shift work or irregular work schedules; nocturnal enuresis, and restless legs syndrome in a mammal, preferably a human, comprising administering to a mammal in need of such treatment an amount of a compound of the formula I, or a pharmaceutically acceptable salt thereof, that is effective in treating such disorder or condition.

The present invention also relates to a pharmaceutical composition for treating a disorder or condition selected from depression, anxiety avoidant personality disorder, premature ejaculation, eating disorders (e.g., anorexia nervosa and bulimia nervosa), migraine, premenstrual syndrome, premenstrual dysphoric disorder, seasonal affective disorder, bipolar disorder, jet lag, sleep disorders such as circadian sleep rhythms disorder, sleep deprivation, REM sleep disorders, hypersomnia, parasomnias, sleep-wake cycle disorders, sleep disorders associated with blindness, sleep disorders associated with obesity, narcolepsy and sleep disorders associated with shift work or irregular work schedules; nocturnal enuresis, and restless legs syndrome in a mammal, preferably a human, comprising a 5HT7 receptor agonizing or partial agonizing effective amount of a compound of the formula I, or a pharmaceutically acceptable salt thereof, and a pharmaceutically acceptable carrier.

The present invention also relates to a method for treating a disorder or condition selected from depression, anxiety avoidant personality disorder, premature ejaculation, eating disorders (e.g., anorexia nervosa and bulimia nervosa), migraine, premenstrual syndrome, premenstrual dysphoric disorder, seasonal affective disorder, bipolar disorder, jet lag, sleep disorders such as circadian sleep rhythms disorder, sleep deprivation, REM sleep disorders, hypersomnia, parasomnias, sleep-wake cycle disorders, sleep disorders associated with blindness, sleep disorders associated with obesity, narcolepsy and sleep disorders associated with shift work or irregular work schedules; nocturnal enuresis, and restless legs syndrome in a mammal, preferably a human, comprising administering to a mammal requiring such treatment a 5HT7 receptor agonizing or partial agonizing effective amount of a compound of the formula I or a pharmaceutically acceptable salt thereof.

Unless otherwise indicated, the term "alkyl", as used herein, may be straight, branched or cyclic, and may include straight and cyclic moieties as well as branched and cyclic moieties.

The term "alkoxy", as used herein, unless otherwise indicated, means "alkyl-O—", wherein "alkyl" is as defined above. Examples of "alkoxy" groups include, but are not limited to, methoxy, ethoxy, propoxy, butoxy and pentoxy.

The term "heteroaryl", as used herein, unless otherwise indicated, includes an aromatic heterocycle containing five or six ring members, of which from 1 to 4 can be heteroatoms selected, independently, from N, S and O, and which rings can be unsubstituted, monosubstituted or disubstituted with substituents selected, independently, from the group consisting of halo, $(C_1-C_4)$alkyl, and $(C_1-C_4)$alkoxy, optionally substituted with from one to three fluorine atoms;

The term "one or more substituents", as used herein, refers to a number of substituents that equals from one to the maximum number of substituents possible based on the number of available bonding sites.

The terms "halo" and "halogen", as used herein, unless otherwise indicated, include, fluoro, chloro, bromo and iodo.

The term "treatment", as used herein, refers to reversing, alleviating, inhibiting the progress of, or preventing the disorder or condition to which such term applies, or one or more symptoms of such condition or disorder. The term "treatment", as used herein, refers to the act of treating, as "treating" is defined immediately above.

Compounds of formula I may contain chiral centers and therefore may exist in different enantiomeric and diastereomeric forms. This invention relates to all optical isomers and all stereoisomers of compounds of the formula I, both as racemic mixtures and as individual enantiomers and diastereoisomers of such compounds, and mixtures thereof, and to all pharmaceutical compositions and methods of treatment defined above that contain or employ them, respectively.

Those compounds of formula I of this invention that possess one or more asymmetric centers are capable of occurring in various stereoisomeric forms or configurations. Hence, the compounds can exist in separated (+)- and (−)-optically active forms, as well as mixtures thereof. The present invention includes all such forms within its scope. Individual isomers can be obtained by known methods, such as optical resolution, optically selective reaction, or chromatographic separation in the preparation of the final product or its intermediate. Individual enantiomers of the compounds of formula I may have advantages, as compared with the racemic mixtures of these compounds, in the treatment of various disorders or conditions.

In so far as the compounds of formula I of this invention are basic compounds, they are capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained. The acids which are used to prepare the pharmaceutically acceptable acid addition salts of the aforementioned base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate))salts.

The present invention also includes isotopically labelled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^2$H, $^3$H, $^{13}$C, $^{11}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

DETAILED DESCRIPTION OF THE INVENTION

Compounds of the formula I may be prepared according to the following reaction schemes and discussion. Unless otherwise indicated, $R^1$, $R^2$, $R^3$, $R^4$, $R^5$, X and Y and structural formula I in the reaction schemes and discussion that follow are as defined above.

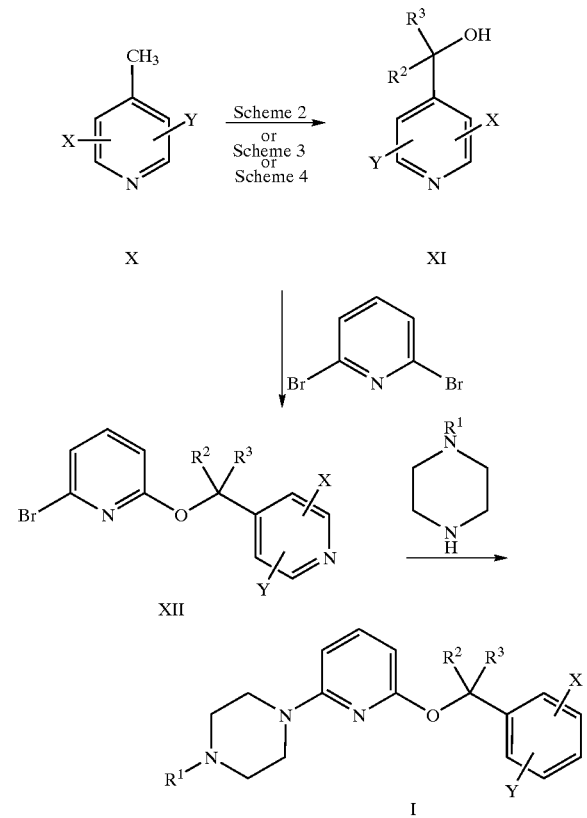

SCHEME 1

SCHEME 2

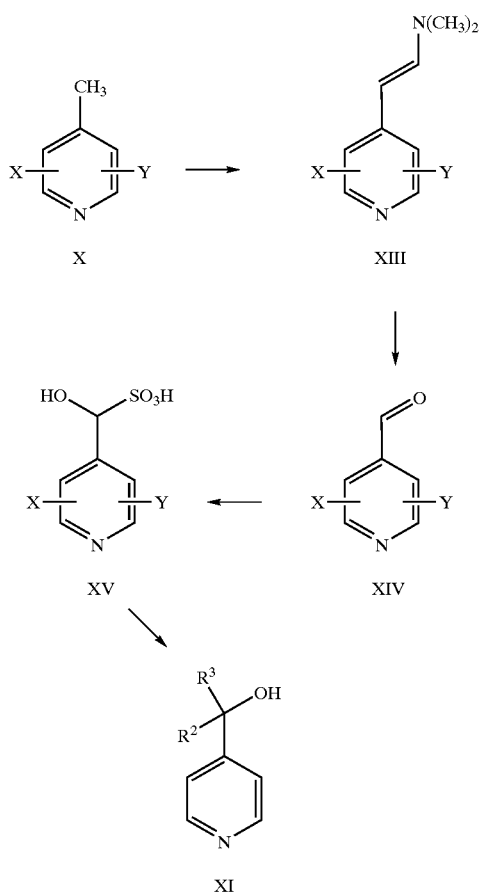

SCHEME 3

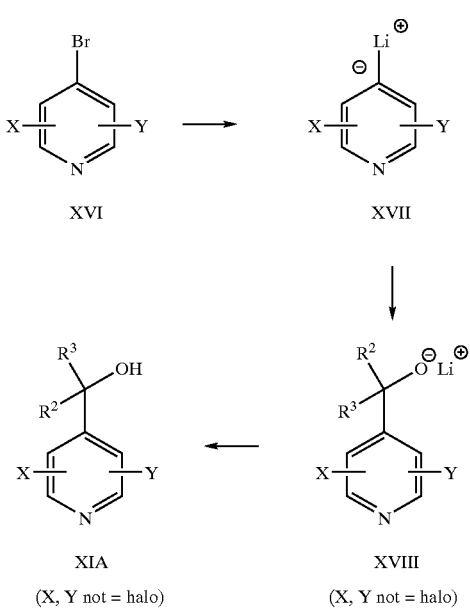

SCHEME 4

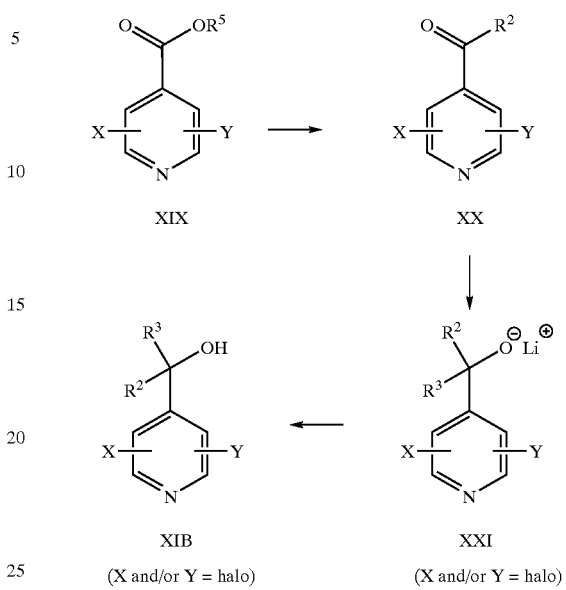

Scheme 1 illustrates a method of preparing compounds of the formula I from compounds of the formula XI. Schemes 2 through 4 illustrate methods of synthesizing the compounds of the formula XI, which are used as starting materials in the methods illustrated in Scheme 1, from the corresponding compounds of formula X. Specifically, Scheme 2 illustrates a method of synthesizing compounds of the formula XI wherein both $R^2$ and $R^3$ are hydrogen (also referred to hereinafter as compounds of the formula XIA), Scheme 3 illustrates a method of synthesizing compounds of the formula XI wherein neither X nor Y is a halo atom (also referred to hereinafter as compounds of the formula XIB), and Scheme 4 illustrates a method of synthesizing compounds of the formula XI wherein one or both of X and Y is a halo atom (also referred to hereinafter as compounds of the formula XIC).

Referring to Scheme 1, reaction of a compound of the formula XI with 2,6-dibromopiperdine in the presence of anhydrous sodium carbonate or anhydrous sodium bicarbonate yields the corresponding compound of formula XII. This reaction is typically conducted in a cyclic ether solvent such as dioxane, THF, ethylene glycol dimethyl ether or ethylene glycol diethyl ether, preferably dioxane or THF at a temperature from about ambient temperature to about the reflux temperature of the solvent, preferably at about the reflux temperature.

The desired compound of formula I can then be obtained by reacting the compound of formula XII with the appropriate compound of the formula

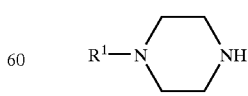

This reaction is typically conducted in a cyclic ether solvent such as those described above for the two foregoing reactions in Scheme 1, preferably dioxane or THF. Suitable reaction temperatures can range from about ambient temperature to about the reflux temperature of the solvent. Preferably, the reaction is run at the reflux temperature.

Referring to Scheme 2, compounds of the formula XIA (R² and R³=hydrogen) are prepared as follows. A compound of the formula X is reacted with a strong base such as sodium or potassium hydride or t-butoxide, a lithium alkyl base or lithium diethyl amide, in a cyclic ether solvent such as dioxane or tetrahydrofuran (THF) or in ethylene glycol dimethyl or diethyl ether, at a temperature from about −78° C. to about room temperature. The resulting anion is then reacted with dimethylformamide (DMF) to yield the enamine intermediate of formula XIII. This intermediate can be oxidatively cleaved with sodium periodate (NaIO₄) to generate the corresponding aldehyde having formula XIV in an inert solvent such as aqueous THF, at a temperature from about −30° C. to about 30° C., preferably at about 0° C. Reaction of the crude aldehyde of formula XIV with aqueous sulfurous acid (H₂SO₃), i.e., saturated aqueous sulfur dioxide (SO₂), at about 0° C. in water or a mixture of a hydroxylic (i.e., an alcoholic) solvent or a water miscible ethereal solvent with water generates the bisulfite adduct of formula XV, generally as a crystalline, white solid, thus facilitating isolation and purification. This bisulfite addition complex can then be conveniently converted to the desired alcohol of formula XIA by the action of sodium borohydride (NaBH₄) in a mixture of alcohol or a water miscible ethereal solvent such as THF or dioxane, and aqueous NaOH.

Referring to Scheme 3, compounds of the formula XIB (neither X nor Y=halo) are prepared as follows. A compound of the formula XVI wherein neither X nor Y is a halo atom is reacted with an alkyl lithium reagent such as n-butyl lithium, sec-butyl lithium, or t-butyl lithium in a cyclic ether solvent such as dioxane or tetrahydrofuran (THF) or in ethylene glycol dimethyl or diethyl ether, at a temperature from about −78° C. to about 0° C., preferably at about −78° C., to yield the corresponding compound having formula XVII. Reaction of the resulting compound of formula XVII, either in situ or following isolation, with a ketone or aldehyde of the formula R²C(=O)R³, at a temperature from about −78° C. to about room temperature, preferably at about 0° C., in the same solvent or a similar solvent to that used to form the compound of formula XVII, yields the corresponding lithium alkoxide of formula XVIII. The compound of formula XVIII can then be converted into the corresponding compound having formula XIB by reacting it with aqueous ammonium chloride or water at a temperature from about 0° C. to about room temperature, preferably at about room temperature.

Referring to Scheme 4, compounds of the formula XIC (one or both of X and Y is a halo atom) are prepared as follows. A carboxylic acid or ester of the formula XIX, wherein one or both of X and Y is a halo atom and wherein R⁵ is hydrogen or (C₁–C₆)alkyl, is reacted with an organometallic compound of the formula LiR² in a cyclic ether solvent such as dioxane or tetrahydrofuran (THF), or in ethylene glycol dimethyl or diethyl ether, at a temperature from about −78° C. to about room temperature, preferably at about 0° C., to produce the corresponding compound of formula XX. Preferably, the reaction mixture is then poured into aqueous ammonium chloride at about 0° C. and the product is isolated. The compound of formula XX is then reacted with an organometallic compound of the formula LiR³, using similar solvents and conditions to those specified above for the reaction with LiR² to yield the corresponding compound of formula XXI. Quenching the compound of formula XXI with aqueous ammonium chloride or water, at a temperature from about 0° C. to about room temperature, preferably at about room temperature, produces the corresponding compound having formula XIC. If R² and R³ are the same, this can be accomplished in one reaction by increasing the amount of the reagent LiR² or LiR³ to two equivalents.

Compounds of the formula I and their pharmaceutically acceptable salts (hereinafter also referred to, collectively, as "the active compounds") are potent partial agonists of the serotonin 7A (5-HT7) receptor. The active compounds are useful in the treatment of depression, anxiety avoidant personality disorder, premature ejaculation, eating disorders (e.g., anorexia nervosa and bulimia nervosa), migraine, premenstrual syndrome, premenstrual dysphoric disorder, seasonal affective disorder, bipolar disorder, jet lag, sleep disorders such as circadian sleep rhythms disorder, sleep deprivation, REM sleep disorders, hypersomnia, parasomnias, sleep-wake cycle disorders, sleep disorders associated with obesity, narcolepsy, sleep disorders associated with blindness, and sleep disorders associated with shift work or irregular work schedules; nocturnal enuresis, and restless legs syndrome.

EXAMPLE I

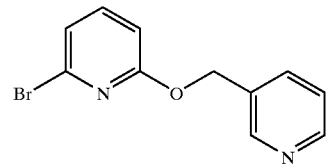

Preparation of
2-bromo-6(pyridin-3-ylmethoxy)-pyridine

A solution of 10.91 g (9.71 mL, 100 mmol) of 3-pyridylcarbinol in 250 mL of THF under N2 was cooled to 0–5° C. in an ice/water bath and then 2.64 g (110 mmol) of oil-free NaH was added portionwise over about 30 min. A white suspension resulted. After 15 min, 23.69 g (100 mmol) of 2,6-dibromopyridine was added and the resulting mixture was refluxed gently overnight under a N2 atmosphere.

The reaction mixture was cooled to room temperature and then poured into ice water. This was extracted three times with EtOAc and the combined EtOAc extracts were washed with saturated NaCl solutions and dried with MgSO4. Evaporation of most of the solvent gave 27.05 g of pale yellow oil.

This oil was dissolved in about 500 mL of ether and a solution of HCl gas in ether was added portionwise. The crystalline solid that separated was filtered off, washed with ether and air-dried to give 12.44 g of the desired product hydrochloride. The filtrate contained additional free base due to not having added enough HCl solution. Thus, the filtrate was concentrated, again dissolved in ether and treated with HCl/ether solution until excess acid had been added. The resulting crystalline solid was filtered, washed with ether and air dried (12.63 g). The two lots of HCl salt were determined to be identical by comparison of their melting points (171–173° C.), their TLC's, their 400 MHz 1H-NMR's and GC-MS retention times and spectra. The two lots were thus combined for total yield of 25.07 g (94.6%). 1H-NMR (CDC13); δ 5.56 (s, 2H), 6.80 (d, J=7 Hz, 1H), 7.13 (d, J=7 Hz, 1H), 7.50 (t,J=Hz, 1), 7.94 (m, 1H), 8.48 (d, J=8 Hz, 1H), 8.71 (m, 1H), 8.88 (s, 1H)

EXAMPLE II

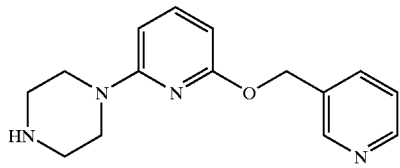

Preparation of
1-[6-(Pyridin-3-ylmethoxy)-pyridin-2-yl]-piperazine

A solution of 2-bromo-6-(pyridin-3-ylmethoxy)-pyridin-hydrochloride prepared as above (25.07 g, 94.6 mmol) was suspended in 275 mL of dry dioxane and then 65.06 g (756.5 mmol, 8 equiv.) of piperazine and 14.19 g (94.6 mmol) of NaI were added. The reaction mixture was then heated slowly to reflux under an atmosphere of dry N2. After about 1 h, the solids in the reaction mixture went partially into solution. Reflux was continued for 48 h at which time the reaction mixture was cooled and taken up in cold water, giving a pale yellow solution. This was extracted four times with ethyl acetate and the combined extracts were back-washed once with water and washed with saturated NaCl solution. The organic solution was dried with MgSO4 and the solvent was evaporated to give 20.7 g of pale yellow oil. This oil was dissolved in 500 mL of dry ether and stirred rapidly while 75 mL of 1 M HCl/ether solution was added dropwise (the mixture was seed with a small amount of mono-HCL salt prepared earlier by the same procedure on smaller scale). The HCl salt crystallized and was granulated overnight at room temperature under N2 atmosphere. The crystalline salt was filtered off and washed with dry ether and dried in a stream of dry N2 and residual ether was removed by pumping in high vacuum for 5 h to give 21.67 g (75%) of off white solid, m.p.=141–143° C.

The affinities of the active compounds for serotonin 7 receptors can be determined using standard radioligand binding assays as described in the literature. The 5-HT7 affinity can be measured using the following procedure.

$^3$H-5-Carboxamidotryptamine ($^3$H-5-CT) Binding to Rat 5HT7 Receptors Expressed in HEK-293 Cells:

Materials:
HEK-293 cells expressing the rat 5-HT7 receptor
Brinkman Polytron Tissue Homogenizer
Phosphate Buffered Saline (GIBCO)
Capped Centrifuge Tubes
Centrifuge
50 mM Tris HCl Buffer, pH 7.7 (SigmaT-4378)
EDTA (Sigma E-4884)
MgSO$_4$ (Sigma M-7506)
CaCl$_2$ (MCBCX156)
pargyline (SigmaP-8013)
ascorbicacid (Calbiochem1831)
5-HTcreatinine sulfate complex (Sigma H-7752)
$^3$H-5CT (Amersham TRK.1038)
12×75 mm boroscilicate glass tubes
96 well V-bottom polypropylene plates (NUNC-442587)
Skatron 96 Well Harvester
Whatman GF/B Glass Fiber Filters (Brandel FP-105) presoaked in 0.3% polyethylenimine (Sigma-P-3143)
Betaplate scintillation counter (Wallac/LKB)

Tissue Preparation

HEK-293 cells expressing rat 5HT7 receptors are grown according to standard cell culture techniques. Cells are harvested by removing the media, rinsing the flasks out with phosphate buffered saline (PBS) and then allowed to sit for 2–3 minutes with PBS containing 2.5 mM EDTA. Cells are dislodged and poured into a RcappableS centrifuge tube. Flasks are rinsed with PBS and added to centrifuge tube. The cells are centrifuged for ten minutes at 40,000×g (20,000 rpm in a Sorvall SS34 rotor). The supernatant is discarded and at this point the remaining pellet is weighed and can be stored frozen (−20 degrees C.) until used in the binding assay. Pellets (fresh or frozen) are homogenized in 50 mM Tris HCl buffer (pH 7.4 at 4 degrees C.) using a Polytron homogenizer (setting 15,000 rpm) for ten seconds in a biological hood certified for use with human tissues. The homogenate is centrifuged for ten minutes at 40,000×g. The supernatant is discarded and the pellet resuspended with the Polytron in a fresh ice-cold 50 mM Tris HCl (pH 7.4 at 4 degrees) buffer and centrifuged again. The final pellet is resuspended in assay buffer (50 mM Tris HCl buffer (pH 7.7 at 25 degrees) containing 0.5 mM EDTA, 10 mM MgSO$_4$, 2 mM CaCl$_2$) for a final tissue concentration of 5–15 mg wet weight of original pellet per mL buffer (2×final concentration).

Receptor Binding

Incubation is initiated by the addition of tissue to V-bottom polypropylene plates (in triplicate). Incubation is at 25 degrees C. for 2 hours.

Each tube receives:

100 uL tissue suspension (5–15 mg/mL original wet weight), 50 uL $^3$H-5-CT** (0.4 nM final concentration), and 50 uL drug or buffer

**$^3$H-5-CT is made up in assay buffer that contains 40 uM pargyline & 0.4% ascorbic acid (for final concentrations of 10 uM pargyline & 0.1% ascorbic acid).

Nonspecific binding is determined using 1 uM 5-HT creatinine sulfate. Incubation is ended by rapid filtration under vacuum through fire-treated Whatman GF/B glass fiber filters (presoaked in 0.3% PEI for two hours and dried) using a 96 well Skatron Harvester (3 sec prewet; 20 seconds wash; 15 seconds dry). Filters are put into LKB sample bags with 10 mL BetaScint. Radioactivity is quantified by liquid scintillation counting using a BetaPlate counter (LKB).

The percent inhibition of specific binding is calculated for each concentration of test compound. An IC50 value (the concentration which inhibits 50% of the specific binding) is determined by linear regression of the concentration-response data (log concentration vs. logit percent values). Ki values are calculated according to Cheng & Prusoff: Ki=IC50/(1+(L/Kd)), where L is the concentration of the radioligand used in the experiment and the Kd value is the dissociation constant for the radioligand determined in separate saturation experiments.

The following assay can be used to evaluate the functional activity of compounds at 5HT7 receptors.

5-HT7 Receptor Mediated Adenylate Cyclase Activity

Materials 1.5 mL siliconized polypropylene microfuge tubes (Costar 3207)
12×75 mm boroscilicate glass tubes
Heated water bath
Glass-Teflon Homogenizer
Centrifuge
HEK-293 cells expressing rat 5-HT7 receptors 32P-ATP (30 Ci/mmol: NEG-003—New England Nuclear)

3H-cAMP (30 Ci/mmol: NET-275—New England Nuclear)

1. Cells are grown according to standard cell culture techniques. Cells are harvested by replacing the media with phosphate-buffered saline containing 2.5 mM EDTA. The cells are homogenized using a hand-held glass-teflon homogenizer. The homogenate is centrifuged at 35,000×g for 10 minutes at 4 degrees C. The pellet is resuspended in 100 mM HEPES buffer containing 1 mM EGTA (pH 7.5) to a final protein concentration of 40 microgram protein per tube.

2. The Reaction Mix is prepared so that the following agents will be at these final concentrations in tube: 4.0 mM $MgCl_2$, 0.5 m MATP, 1.0 m McAMP, 0.5 mM IBMX, 10 mM, phosphocreatine, 0.31 mg/mL creatine phosphokinase, and 100 uM GTP0.5–1 microcuries a-[$^{32}$P]-ATP per tube.

3. Incubation is initiated by the addition of tissue to siliconized microfuge tubes (in triplicate). Incubation is at 37° C. for 15 minutes.

Each tube receives:

20 uL tissue, 20 uL drug or buffer (at 5× final concentration), 20 uL 100 nM agonist or buffer (at 5× final concentration), and 40 uL Reaction Mix 4. Incubation is terminated by the addition of 100 uL 2% SDS, 1.3 mM cAMP, 45 mM ATP solution containing 40,000 dpm [$^3$H]-cAMP to monitor the recovery of cAMP from the columns. The separation of [$^{32}$P]-ATP and [$^{32}$P]-cAMP is accomplished using the method of Salomon et al., *Analytical Biochemistry* 58: 541–548, 1974, which is incorporated herein by reference in its entirety. Radioactivity is quantified by liquid scintillation counting.

The maximal effect of agonists is defined in terms of the maximal effect of serotonin (5-HT). Antagonists are evaluated by their ability to inhibit 5HT-stimulated adenylate cyclase activity. IC50 values are converted to apparent Ki values by the following equation: IC50/(1+([agonist]/EC50 of agonist)).

Activity of the active compounds as antidepressants and related pharmacological properties can be determined by methods (1)–(4) below, which are described in Koe, B. et al., *Journal of Pharmacology and Experimental Therapeutics*, 226 (3), 686–700 (1983), which is incorporated herein by reference in its entirety. Specifically, activity can be determined by studying (1) their ability to affect the efforts of mice to escape from a swim-tank (Porsolt mouse "behavior despair" test), (2) their ability to potentiate 5-hydroxytryptophan-induced behavioral symptoms in mice in vivo, (3) their ability to antagonize the serotonin-depleting activity of p-chloroamphetamine hydrochloride in rat brain in vivo, and (4) their ability to block the uptake of serotonin, norepinephrine and dopamine by synaptosomal rat brain cells in vitro. The ability of the active compounds to counteract reserpine hypothermia in mice in vivo can be determined according to the methods described in U.S. Pat. No. 4,029,731, which is incorporated herein by reference in its entirety.

What is claimed is:

1. A compound selected from the following compounds and their pharmaceutically acceptable salts:

1-[6-(Pyridin-4-ylmethoxy)-pyridin-2-yl]-piperazine;
3-{4-[6-(Pyridin-4-ylmethoxy)-pyridin-2-yl]-piperazin-1-yl}-propan-1-ol;
1-Methyl-4-[6-(pyridin-4-ylmethoxy)-pyridin-2-yl]-piperazine;
1-Ethyl-4-[6-(pyridin-4-ylmethoxy)-pyridin-2-yl]-piperazine;
1-Benzyl-4-[6-(pyridin-4-ylmethoxy)-pyridin-2-yl]-piperazine;
1-Propyl-4-[6-(pyridin-4-ylmethoxy)-pyridin-2-yl]-piperazine;
1-(2-Methoxy-ethyl)-4-[6-(pyridin-4-ylmethoxy)-pyridin-2-yl]-piperazine;
1-Benzo[1,3]dioxol-5-ylmethyl-4-[6-(pyridin-4-ylmethoxy)-pyridin-2-yl]-piperazine;
1-(2-Phenoxy-ethyl)-4-[6-(pyridin-4-ylmethoxy)-pyridin-2-yl]-piperazine;
1-(3-Phenoxy-propyl)-4-[6-(pyridin-4-ylmethoxy)-pyridin-2-yl]-piperazine;
1-(3-Phenyl-propyl)-4-[6-(pyridin-4-ylmethoxy)-pyridin-2-yl]-piperazine;
1-Butyl-4-[6-(pyridin-4-ylmethoxy)-pyridin-2-yl]-piperazine;
3-{4-[6-(Pyridin-4-ylmethoxy)-pyridin-2-yl]-piperazin-1-yl}-propionitrile-;
4-{4-[6-(Pyridin-4-ylmethoxy)-pyridin-2-yl]-piperazin-1-yl}-butyronitrile;
1-(3-Methyl-benzyl)-4-[6-(pyridin-4-ylmethoxy)-pyridin-2-yl]-piperazine;
1-(3-Chloro-benzyl)-4-[6-(pyridin-4-ylmethoxy)-pyridin-2-yl]-piperazine;
3-{4-[6-(Pyridin-4-ylmethoxy)-pyridin-2-yl]-piperazin-1-ylmethyl}-benzonitrile;
2-{4-[6-(Pyridin-4-ylmethoxy)-pyridin-2-yl]-piperazin-1-ylmethyl}-benzonitrile;
4-{4-[6-(Pyridin-4-ylmethoxy)-pyridin-2-yl]-piperazin-1-ylmethyl}-benzonitrile;
1-(3-Fluoro-benzyl)-4-[6-(pyridin-4-ylmethoxy)-pyridin--2-yl]-piperazine; 1-(4-Fluoro-benzyl)-4-[6-(pyridin-4-ylmethoxy)-pyridin-2- -yl]-piperazine;
1-(3-Methoxy-benzyl)-4-[6-(pyridin-4-ylmethoxy)-pyridin-2- -yl-piperazine; 1-(2-Chloro-benzyl)-4-[6-(pyridin-4-ylmethoxy)-pyridin-2-y-1]-piperazine;
1-(4-tert-butyl-benzyl)-4-[6-(pyridin-4-ylmethoxy)-pyridin-2-yl]-piperazine; 1-(2-Fluoro-benzyl)-4-[6-(pyridin-4-ylmethoxy)-pyridin-2- -yl]-piperazine;
1-(2-Bromo-benzyl)-4-[6-(pyridin-4-ylmethoxy)-pyridin-2-y-1]-piperazine;
1-Isopropyl-4-[6-(pyridin-4-ylmethoxy)-pyridin-2-yl]-piperazine;
1-Cyclopropyl-4-[6-(pyridin-4-ylmethoxy)-pyridin-2-yl]-piperazine;
1-(1-Methyl-hexyl)-4-[6-(pyridin-4-ylmethoxy)-pyridin-2-yl]-piperazine;
1-[6-(2-Methyl-pyridin-4-ylmethoxy)-pyridin-2-yl]-piperazine; 4-(6-Piperazin-1-yl-pyridin-2-yloxymethyl)-quinoline;
1-[6-(3-Methyl-pyridin-4-ylmethoxy)-pyridin-2-yl]-piperazine;
1-[6-(2-Phenyl-pyridin-4-ylmethoxy)-pyridin-2-yl]-piperazine;
1-[6-(2,6-Dimethyl-pyridin-4-ylmethoxy)-pyridin-2-yl]-piperazine; and
1-(4-Fluoro-benzyl)-4-[6-(pyridin-4-ylmethoxy)-pyridin-2-yl]-piperazine.

* * * * *